(12) United States Patent
Tanugula et al.

(10) Patent No.: US 9,943,991 B2
(45) Date of Patent: Apr. 17, 2018

(54) MOLD WITH SEPARABLE FEATURES

(71) Applicant: Align Technology, Inc., San Jose, CA (US)

(72) Inventors: Rohit Tanugula, San Jose, CA (US); Dennis Te, San Jose, CA (US); Peter Webber, Lafayette, CA (US); Shiva P. Sambu, Milpitas, CA (US); Crystal Tjhia, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 323 days.

(21) Appl. No.: 14/716,607

(22) Filed: May 19, 2015

(65) Prior Publication Data

US 2015/0336299 A1 Nov. 26, 2015

Related U.S. Application Data

(60) Provisional application No. 62/001,489, filed on May 21, 2014.

(51) Int. Cl.
| | |
|---|---|
| *B29C 33/44* | (2006.01) |
| *B29C 33/50* | (2006.01) |
| *B29C 51/34* | (2006.01) |
| *A61C 7/08* | (2006.01) |
| *B29L 31/00* | (2006.01) |
| *B33Y 80/00* | (2015.01) |
| *B33Y 10/00* | (2015.01) |

(52) U.S. Cl.
CPC .............. *B29C 33/448* (2013.01); *A61C 7/08* (2013.01); *B29C 33/50* (2013.01); *B29C 51/34* (2013.01); *B29L 2031/753* (2013.01); *B29L 2031/757* (2013.01); *B33Y 10/00* (2014.12); *B33Y 80/00* (2014.12)

(58) Field of Classification Search
None
See application file for complete search history.

(56) References Cited

U.S. PATENT DOCUMENTS

| | | |
|---|---|---|
| 2001/0002014 A1 | 5/2001 | Champagnon et al. |
| 2004/0191728 A1 | 9/2004 | Miller |
| 2008/0233528 A1* | 9/2008 | Kim ...................... A61C 7/146 433/2 |
| 2011/0304075 A1 | 12/2011 | Catoen et al. |

FOREIGN PATENT DOCUMENTS

WO 00/32132 A1 6/2000

OTHER PUBLICATIONS

"Malocclusion." Merriam-Webster.com. Merriam-Webster, n.d. Web. Aug. 18, 2017 accessed at merriam-webster.com on Aug. 17, 2017.*

(Continued)

*Primary Examiner* — Alison L Hindenlang
*Assistant Examiner* — Jamel M Nelson
(74) *Attorney, Agent, or Firm* — Lowenstein Sandler LLP

(57) ABSTRACT

A mold comprises a main body and a separable feature. One or more weakened regions join the separable feature to the main body. The one or more weakened regions are breakable to enable the main body to be removed from a shell independently of the separable feature after the shell is formed over the mold.

10 Claims, 10 Drawing Sheets

(56) References Cited

OTHER PUBLICATIONS

Written Opinion of the International Preliminary Examining Authority for PCT Application No. PCT/IB2015/000743 dated Apr. 28, 2016.
Bjorn, Ludwig et al. "Selbstligierende Brackets: Konzepte und behandlung" machine translated as "Self-ligating Brackets: Concepts and Treatment", Dec. 16, 2009, pp. 94-96, Thieme Verlag, XP055205560, ISBN: 78-3-13-149701-7; includes a German transcription and machine translation of the referenced pages.
Ludwig Bjorn et al, "Selbstligierende Brackets: Konzepte und Behandlung" Dec. 16, 2009, pp. 94-96, Thieme Verlag, Germany, XP055205560, ISBN: 978-3-13-149701-7.
International Search Report and Written Opinion in PCT Application No. PCT/IB2015/000743 dated Aug. 12, 2015.

\* cited by examiner

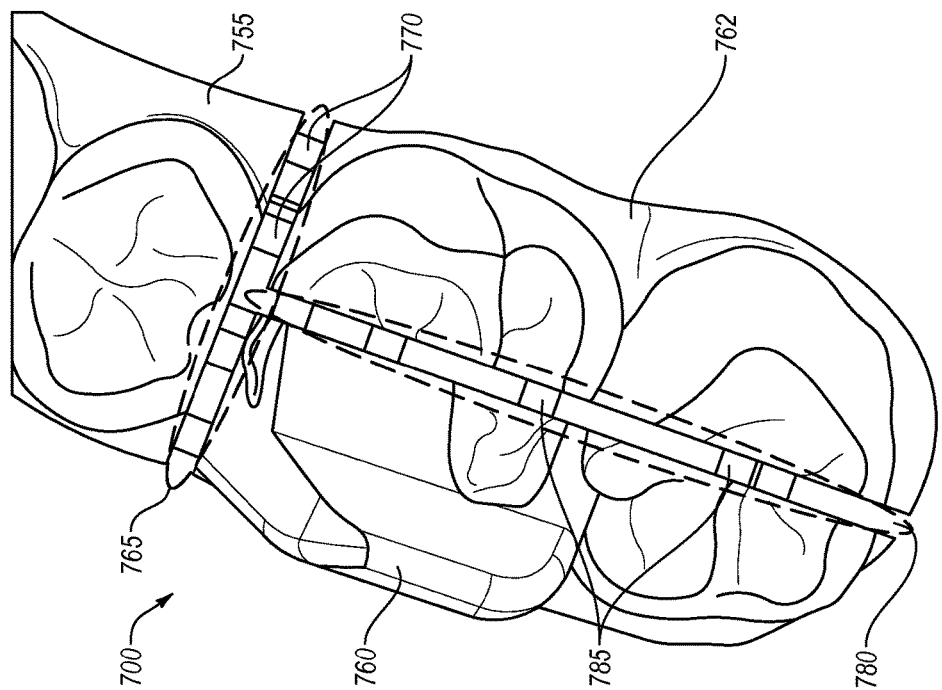
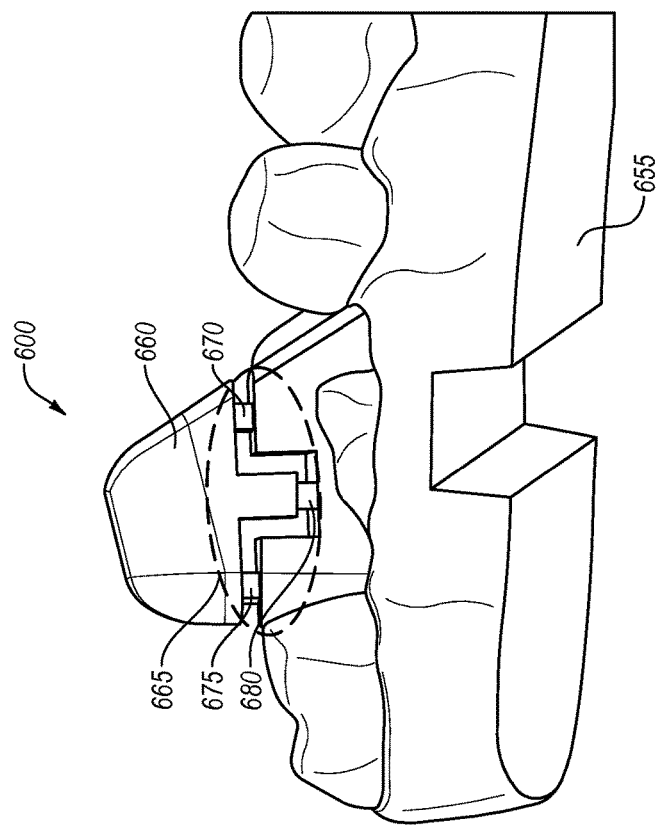

MOLD WITH SEPARABLE FEATURES

RELATED APPLICATIONS

This patent application claims the benefit under 35 U.S.C. § 119(e) of U.S. Provisional Application No. 62/001,489, filed May 21, 2014, which is herein incorporated by reference.

TECHNICAL FIELD

Embodiments of the present invention relate to the field of rapid prototyping molds and, in particular, to a mold with separable features formed using a rapid prototyping technique.

BACKGROUND

For some applications, shells are formed around molds to achieve a negative of the mold. The shells are then removed from the molds to be further used for various applications. One example application in which a shell is formed around a mold and then later used is corrective dentistry or orthodontic treatment. In such an application, the mold is of a dental arch for a patient and the shell is an aligner to be used for aligning one or more teeth of the patient.

One challenge with molds used to form shells is the subsequent removal of the sheds from the molds. In order to ensure that a shell will be removable from a mold without damaging or permanently deforming the shell, the shapes and types of features that are included in the mold may be limited. For example, features with significant undercuts (also referred to as negative inclination) and/or complex features may impair the removal of the shell from the mold.

BRIEF DESCRIPTION OF THE DRAWINGS

The present invention is illustrated by way of example, and not by way of limitation, in the figures of the accompanying drawings.

FIG. 6 illustrates another example mold with a separable feature, in accordance with one embodiment.

FIG. 7 illustrates an example breakable mold, in accordance with one embodiment.

DETAILED DESCRIPTION

Figure 1:
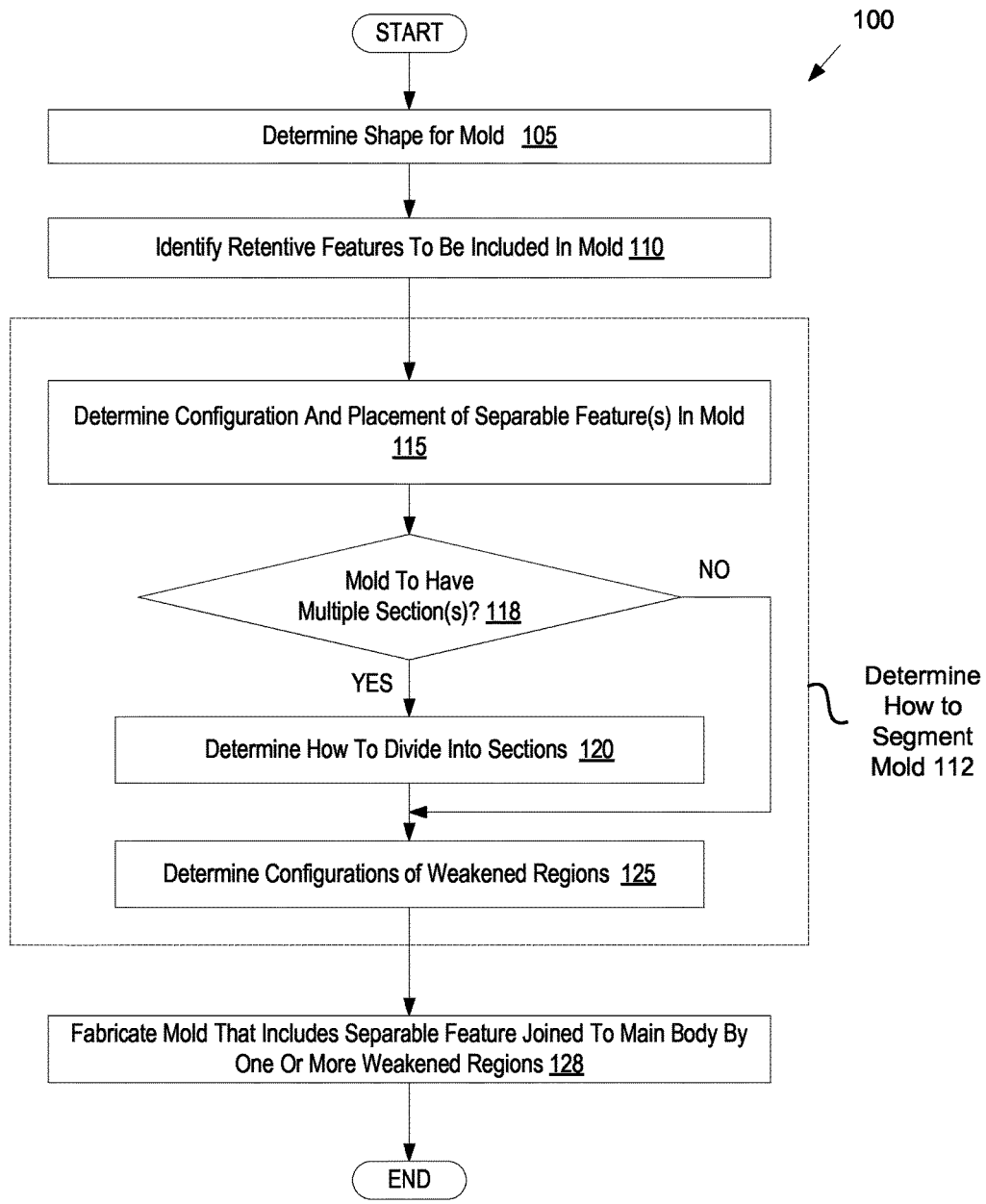
FIG. 1 illustrates a flow diagram for a method of fabricating a mold with a separable feature, in accordance with one embodiment.

Described herein are embodiments of molds with separable features and methods of manufacturing and using such molds. Molds having separable features may be designed, fabricated and used. The separable features may be joined to a main body of the mold by weakened regions. The separable features may be formed at areas of the mold that would otherwise be retentive features (e.g., features with undercuts or negative inclinations). The mold may also have a segmented configuration that includes multiple segments of the main body, where the segments are joined together by additional weakened regions. For example, a breakable or deflectable mold may be sectioned into two or more weakly joined sections. The mold may be broken or deflected at the weakened regions that join the separable feature to the main body and/or that connect different segments during the forming of a shell on the breakable mold or after the shell has been formed on the mold (e.g., during removal of the shell from mold). After the mold is broken at the weakened regions, the separable feature may be removed from the shell separately from the main body of the mold. If the mold is also divided into multiple sections joined by additional weakened regions, the breaking or deflecting of the additional weakened regions causes the mold to be at least partially separated into the constituent sections (e.g., fully separated for a breakable mold or partially separated for a deflectable mold). In some instances, one or more sections may not completely separate from the shell and/or other sections of the mold. For example, a section may mostly separate from another section, but leave a point of connection. This may permit additional deflection and/or freedom for the shell to be removed without damage. Each of the sections may then be removed from the shell independently of the other sections.

Use of a mold with separable features in accordance with embodiments herein enables complex features (e.g., features with a rough surface texture), bulky features (e.g., features for which an aspect ratio of the main body to at least one dimension of the feature is skewed), features with significant undercuts and/or other retentive features to be incorporated into formed shells. For example, if the mold is of a dental arch for a patient and the shell is an orthodontic aligner to be used for aligning one or more teeth of the patient, then the mold enables the aligner to correct dental/orthodontic problems such as very crowded teeth, proclined teeth, retroclined teeth, ectopic teeth, out of arch teeth, and so on. Use of a mold with separable features also makes removal of the shell from the mold easier in other instances. The shell may also be an orthodontic retainer or an orthodontic splint to be used for at least one of retaining or positioning one or more teeth of the patient. The term aligner is used herein to refer to an orthodontic aligner, retainer and/or splint that can perform one or more of aligning teeth, retaining teeth and positioning teeth. Without the mold with the separable feature, the ability to create aligners with complex features that can facilitate correction of such dental/orthodontic problems can be impaired. Additionally, use of molds with separable features as described herein enables enhanced features with moderate to significant undercuts to be placed on a patient's teeth (and included in the mold). Such enhanced features may facilitate dental correction by enabling the treatment of different and/or complex dental problems. Moreover, use of the mold with separable features may minimize or eliminate damage caused to shells during removal of the molds from the shells, thereby reducing an amount of scrapped product and therefore overall cost.

Molds with separable features of dental arches for the production of orthodontic aligners are described with reference to various embodiments herein. However, it should be understood that molds described herein may also be produced for other purposes (e.g., for molding any other desired plastic item).

Embodiments are discussed herein with reference to molds with separable features, and to forming shells over such molds. Such molds include a main body (which may or may not be divided into sections) joined to a separable feature by a weakened region that can break prior to removal of a shell from the molds. For embodiments in which the main body is divided into multiple sections, those sections may be breakable or deflectable from one another. For example, the weakened regions joining the segments may bend or deflect during removal of the shell from the mold. This deflection of the weakened regions may enable the mold to be removed from the shell in spite of features in the deflectable mold that include negative inclination or an undercut. For example, a practitioner may apply a force to a first section of the deflectable mold that deflects a weakened region connecting a first section to a second section, thereby causing the first section to partially separate from the second section. This force may cause the first section to be substantially removed or separated from the shell before the second section begins to separate from the shell.

FIG. 1 illustrates a flow diagram for a method 100 of fabricating a mold having one or more separable features, in accordance with one embodiment. In some embodiments, one or more operations of method 100 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 100 may be performed by a mold modeling module such as mold modeling module 850 of FIG. 8. Additionally, some operations may be performed by a fabrication machine based on instructions received from processing logic. Some operations may alternately be performed by a user (e.g., based on user interaction with a mold modeling module or drafting program).

At block 105 of method 100, a shape of a mold is determined. In one embodiment, the shape is determined based on a scan of an object to be modeled. In the example of orthodontics, an intraoral scan of a patient's dental arch may be performed to generate a three dimensional (3D) virtual model of the patient's dental arch. For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled. The negative mold may then be scanned to determine a shape of a positive mold that will be produced.

Referring back to the example of orthodontics, multiple different molds may be generated for a single patient. A first mold may be a model of a patients dental arch and/or teeth as they presently exist, and a final mold may be a model of the patient's dental arch and/or teeth after correction of one or more teeth and/or a jaw. Multiple intermediate molds may be modeled, each of which may be incrementally different from previous molds. Aligners may be formed from each mold to provide forces to move the patients teeth. The shape of the final mold and each intermediate mold may be determined by computing the progression of tooth movement throughout orthodontic treatment from initial tooth placement and orientation to final corrected tooth placement and orientation. Each mold may be used to fabricate an aligner that will apply forces to the patients teeth at a particular stage of the orthodontic treatment.

A shell can be designed to contain features (bumps, protrusions, wings, etc.) that are non-natural to the patient's dentition. These features may facilitate the application of particular desired forces to reposition teeth or position the jaw. These features may be included in the shape of the mold in order to manufacture the aligner shell.

In some instances, a dental practitioner may form attachments or features on some of a patient's teeth. These additional non-naturally occurring features may be used to facilitate the application of particular desired forces on the patient's teeth to reposition the teeth (e.g., to rotate and or move the teeth). The features may also apply forces to facilitate jaw movement. These attachments or features may include small, medium and large bumps, protrusions, wings, etc. that are formed from a hard composite material that adheres to the patient's teeth. Such features may be included in the determined shape of the mold. For example, these features may be placed before the dental arch of the patient is scanned, and thus may be reflected in a 3D virtual model of the dental arch.

Additionally, or alternatively, features can be added in a model (e.g., a 3D model generated based on a 3D intraoral scan of a patient's jaw or other dental site). The mold with separable features generated from the model would then include the features even if those features are not present in the patient's mouth. Accordingly, features can be added before or after intraoral scanning is performed.

At block 110, one or more retentive features of the determined shape for the mold that have complex shapes, bulky shapes, undercuts and/or other retentive properties are identified. A retentive feature (feature having retentive properties) is a feature that will hinder removal of a shell formed over the mold from the mold. As used herein, the term bulky feature refers to a feature of a mold having an aspect ratio to a main body of the mold that is skewed in terms of at least one of height, width or length. In one embodiment, a skewed aspect ratio is an aspect ratio that is at least 30% larger. For example, a feature may be determined to be a bulky feature if it has a height, width or length that is at least 30% larger than an average height, width or length of the mold.

In one embodiment, processing logic identifies such features. For example, processing logic may process a 3D virtual model to identify all features having undercuts that meet some threshold. The threshold may be a particular amount of undercut (e.g., 0.2 mm of undercut, 0.4 mm of undercut, 1.0 mm of undercut, etc.) or a particular aspect ratio. Additionally, multiple different thresholds may be used to identify features that might be problematic. Alternatively or additionally, a dental practitioner may identify complex features, features with undercuts and/or other retentive features. For example, the dental practitioner may highlight or delineate such features on a 3D virtual model using a drawing tool and/or a computer aided drafting application (e.g., using a model modeling module). Some examples of notable features that might have undercuts that are pronounced enough to cause problems include attachments placed by the dental practitioner, crowded teeth, proclined teeth, retroclined teeth, ectopic teeth, out of arch teeth, and so on.

At block 112, a determination is made of how to segment the virtual 3D mold to form a mold with one or more separable features and/or with breakable or deflectable segments. In one embodiment, such a determination is made by processing logic. This may include determining configuration and placement of separable features in the mold (block 115), determining whether the mold is to have multiple sections (block 118), determining how to divide the mold into sections (block 120), and/or determining configurations of weakened regions (block 125).

In one embodiment, at block 115 processing logic (or a dental practitioner assisted by processing logic) may determine a shape of a separable feature and how that separable feature is to be joined to a main body of a mold. Processing logic or the dental practitioner may determine whether the mold is to be a contiguous structure that includes both the separable feature and the main body, or whether the main body is to be a first mold and the separable feature is to be a separate second mold that is attached to the first mold. In one embodiment, the separable feature is to be completely surrounded by weakened regions that join the separable feature to the main body.

At block 118, processing logic or the dental practitioner determines whether the mold is to have multiple sections. A mold with separable features may be divided into multiple sections to further reduce stress that will be imparted on a shell formed over the mold during removal of the shell from the mold. For example, a mold may be separated into a right segment and a left segment, and each of the right segment and the left segment may include a distinct separable feature. If the mold is to be divided into multiple sections, the method continues to block 120. Otherwise the method proceeds to block 125.

At block 120, processing logic (or the dental practitioner) may determine where to place weakened regions. The weakened region placement may be determined relative to the separable features, and may divide the virtual 3D mold into multiple sections that are joined by the weakened regions. In a simple example, a mold may be divided into two sections, where a first section is on a first side of a separable feature and a second section is opposite the first section relative to the separable feature (e.g., on an opposite side of the feature). In another simple example, a mold may be divided into two sections, where a first section includes a separable feature and a second section does not include a separable feature or includes another separable feature.

At block 125, the processing logic or a technician may determine configurations for the weakened regions that are to join the sections of the mold and/or that are to join separable features to a main body of the mold. This may include determining the shapes of the weakened regions and strengths of the weakened regions (e.g., that control how much force is necessary to break the weakened region) as well as how each of the weakened regions is to be weakened, if the mold is to be a single contiguous mold, processing logic or the dental practitioner may determine configurations for weakened regions that join the separable feature to the main body. If the mold is to be multiple separate molds, processing logic or the dental practitioner may determine a shape and configuration of a receiving element in the first mold of the main body that is to receive an attachment element of the second mold of the separable feature.

Weakened regions may be achieved based on at least one of a weakening geometry, weakening build parameters, or materials that introduce weakening. For example, the strength of a weakened region may be controlled by modifying the length, width, height and/or number of support structures (e.g., support struts) that are included in a weakened region. The locations, dimensions, and strengths of the weakened regions may be important to the function of the mold. In one embodiment, the weakened regions may be designed to withstand the forces and stresses of thermoforming or pressure forming, while also being weak enough to later break apart when manually manipulated by a technician or computer controlled robotic manipulator. Additionally, the weakened regions may be configured such that they will not materially affect a final shape of the shell (e.g., cause imperfections or undesirable artifacts in a region of the shell formed over the weakened region such as seepage of the shell into a gap included in the weakened region). For example, the portion of the weakened region that will interface with the shell may be solid (e.g., in the example of weakened region that includes a cut or gap that does not extend to one surface of the mold). In other words, the weakened region may include a void or a cut at a cross section between two sections in the mold (and/or between a separable feature and a main body of the mold) that extends through less than an entirety of the mold at the cross section. In another example, a gap or void between two sections (and/or between a separable feature and a main body of the mold) may extend to the surface of the mold that interfaces with the shell, but the gap may be narrow enough so as not to cause artifacts in the shell formed on the mold.

In an example, one type of weakened region is a cut that extends most of the way through the mold. The cut may extend close to, but not penetrate, an upper surface of the mold that will contact a shell. Another type of weakened region is a void separating two sections with one or multiple support structures that bridge the void. Another type of weakened region is a series of perforations between two or more sections. Other types of weakened regions are also possible:

In some embodiments, the mold is manufactured as two or more separate molds (e.g., one mold for the main body and additional molds for each separable feature) that are joined after their manufacture. In such embodiments, the weakened region may be a contact point between the different molds. In one embodiment, the weakened region is an adhesive (e.g. glue, double sided tape, solder, weld, etc.) that joins the main body to the separable features. In another embodiment, the weakened region is a mechanical fixture or element that secures the separable feature to the main body. For example, the weakened region may include a protrusion from a separable feature that extends into a depression (i.e. receiving element) in the main body. Other types of weakened regions may also be used.

At block 128, the mold with separable features is fabricated. This may include forming a single mold having a main body joined to one or more separable features by weakened regions or forming multiple separate molds that are then joined together by weakened regions. In one embodiment, the mold is fabricated based on a 3D virtual model of the mold. In one embodiment, the 3D virtual model includes a main body and one or more separable features joined by weakened regions. The 3D virtual model may additionally include multiple sections as well as weakened regions that join these sections. Accordingly, the mold may be manufactured as a single uniform body with these sections, main body, separable features and weakened regions built into the design of the mold. Alternatively, or additionally, one or more weakened regions may be introduced to the mold and/or the mold may be divided into one or more sections via a post processing procedure. For example, one or more cuts, perforations, holes, etc, may be formed in the mold using a saw, a drill, a laser cutter, a plasma cutter, a knife, etc. after the mold has been formed. Alternatively, multiple molds may be created (one for the main body and one for each separable feature), and the multiple molds may subsequently be joined (e.g., via glue, mechanical retention mechanisms, adhesives, etc.).

In one embodiment, the mold (or molds) is fabricated using a rapid prototyping manufacturing technique. One example of a rapid prototyping manufacturing technique is 3D printing, 3D Printing includes any layer-based additive manufacturing processes. A 3D printer may receive an input of the 3D virtual model of the mold with separable features (e.g., as a computer aided drafting (CAD) file or 3D printable file such as a stereolithooraphy (STL) the), and may use the 3D virtual model to create the mold. 3D printing may be achieved using an additive process, where successive layers of material are formed in proscribed shapes, 3D printing may be performed using extrusion deposition, granular materials binding, lamination, photopolymerization, or other techniques.

In one embodiment, stereolithography (SLA), also known as optical fabrication solid imaging, is used to fabricate an SLA mold. In SLA, the mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Each layer may have a thickness of between 25 microns and 200 microns in embodiments. Once all of the layers of the mold are formed, the mold may be cleaned and cured.

In one embodiment, the mold is generated as multiple separate molds that are then joined together. In such an embodiment, two or more sections may be manufactured as separate molds. These separate molds may then be joined together in a manner that enables them to later deflect from one another or break apart. Thus, the intersections between the separate molds/sections may form the weakened regions. In one example, different sections (and/or a separable feature and a main body) are joined by an elastic or flexible glue to enable deflection. In another example, different sections (and/or a separable feature and a main body) are joined by a relatively weak glue that will stop securing the sections together when sufficient force is applied (e.g., during removal of a shell from the mold). In another example, the different sections (and/or a separable feature and a main body) interlock in a manner such that they are separable when appropriate force is applied.

Figure 2:
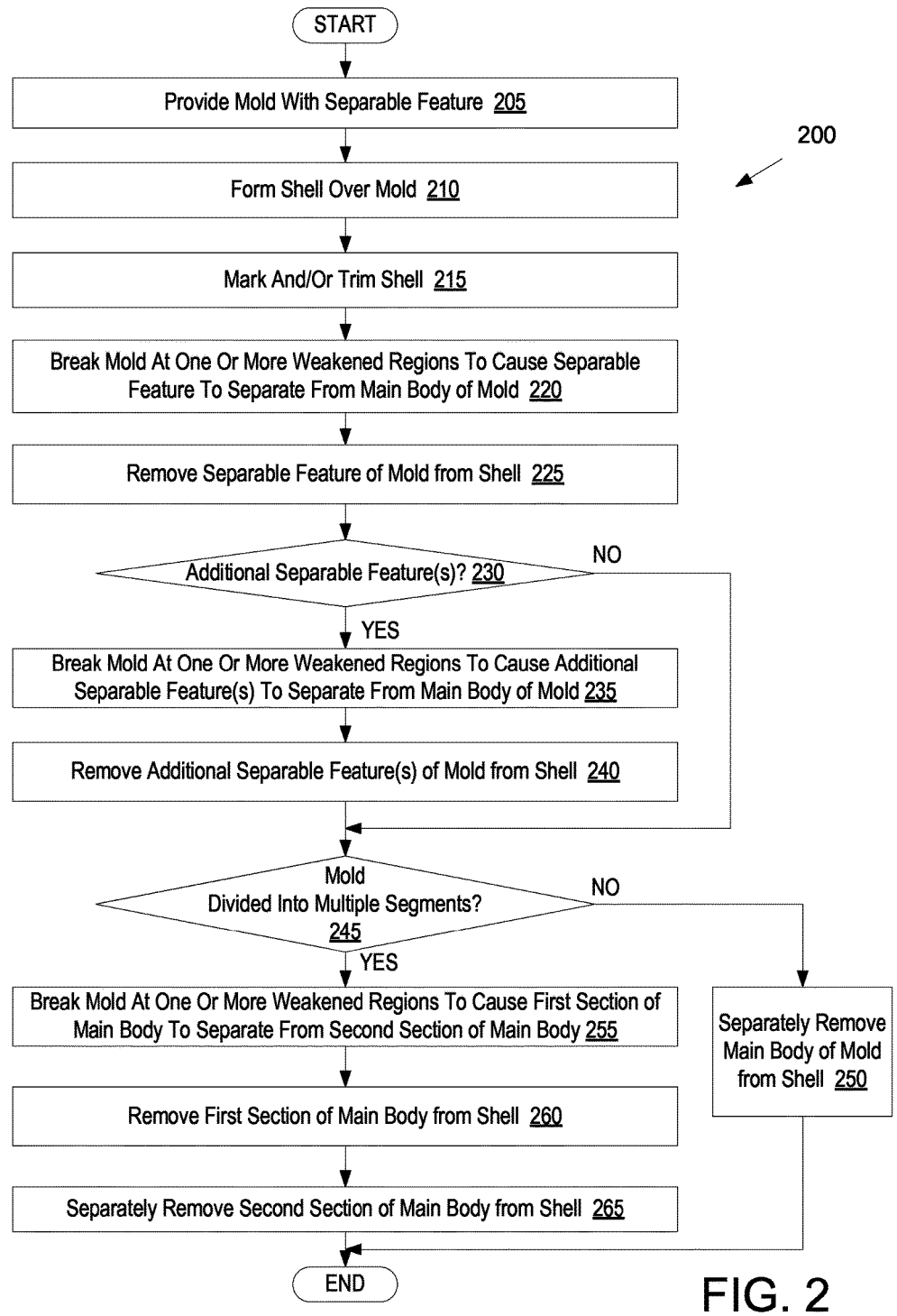
FIG. 2 illustrates a flow diagram for a method of using a mold with a separable feature to fabricate a shell, in accordance with one embodiment.

FIG. 2 illustrates a flow diagram for a method 200 of using a mold with separable features to fabricate a shell, in accordance with one embodiment. At block 205 of method 200, a mold with separable features is provided. The mold may have been manufactured in accordance with method 100 of FIG. 1. The mold includes at least a separable feature joined to a main body by a weakened region. The mold may also include any number of sections in one embodiment, and may include weakened regions at each intersection of two or more sections. The separable feature may attach to one or more of the sections. If the mold is a combination of a main body mold and one or more separable feature molds, then the separable feature molds may be attached to the main body mold by weakened regions at block 205. The placement of weakened regions around a separable feature and/or between sections may be to accommodate retentive features in the mold (e.g., those features having undercuts or negative inclination).

At block 210, a shell is formed over the mold. In one embodiment, a sheet of material is pressure formed or thermoformed over the mold. The sheet may be, for example, a sheet of plastic (e.g., an elastic thermoplastic). To thermoform the shell over the mold, the sheet of material may be heated to a temperature at which the sheet becomes pliable. Pressure may concurrently be applied to the sheet to form the now pliable sheet around the mold with the separable feature. Once the sheet cools, it will have a shape that conforms to the mold. In one embodiment, a release agent (e.g., a non-stick material) is applied to the mold before forming the shell. This may facilitate later removal of the mold from the shell.

At block 215, the shell may be marked and/or trimmed while it is still on the mold. For example, if the mold is of a dental arch and the shell is an orthodontic aligner to align a patient's teeth, then a gingival cut line (or other cut line) may be identified and cut. A laser cutter, plasma cutter, or mechanical cutter (e.g. a 5 axis milling machine) may be used to cut the gingival cut line or other cut line. In one embodiment, the aligner is not cut until after the shell is removed from the mold. Alternatively, the aligner may be cut prior to removal of the mold. Alternatively, some trimming may occur before removal of the mold from the shell and additional trimming may occur after the removal of the mold from the shell. Marking of the shell may include using a laser to add a label such as a serial number or part number to the shell.

At block 220, the mold is broken at the one or more weakened regions to cause the separable feature to separate from the main body of the mold. The weakened regions may be manually broken by a technician or by an automated tool. In one embodiment, ultrasonic waves may be applied to the breakable mold to collapse, crumble or otherwise break the weakened regions. Alternatively, the mold may be vibrated to break the weakened regions. In another example, a fixture with a knife edge or other shaped edge may be applied to the breakable structure (e.g., at a weakened region) to crush, cut or otherwise break one or more of the weakened regions. The fixture may apply a predetermined amount of force in a particular direction or angle to break the weakened regions, for example. In another example, the weakened regions may be crushed by applying pressure to the mold. In another example, the weakened regions are broken by application of a force to remove the mold from the shell.

If there are multiple weakened regions, then all of the weakened regions may be broken approximately simultaneously (e.g., in response to a single application of force to the breakable mold). Alternatively, different weakened regions may be broken at different times. For example, a first application of force may break a first subset of weakened regions, and a second application of force may break a second subset of weakened regions.

At block 225, the separable feature of the breakable mold is removed from the shell. The main body may later be removed from the shell. In one embodiment, the weakened region completely surrounds the separable feature and is accessible from a bottom of the mold. An example of this is shown in FIG. 3B. This enables a technician or machine to break the mold at the weakened region from the bottom of the mold, and then extract the separable feature from beneath the mold while the main body of the mold is still attached to the shell. Alternatively, the main body may first be removed from the shell, followed by a later removal of the separable feature from the shell.

At block 230, processing logic or a technician determines whether there are additional separable features in the mold. If there are additional separable feature, the method continues to block 235. Otherwise, the method proceeds to block 245.

At block 235, the mold is broken at one or more weakened regions joining an additional separable feature to the main body to cause the additional separable feature to separate from the main body of the mold. At block 240, the additional separable feature is removed from the shell. This process may be performed for each additional separable feature on the mold.

At block 245, processing logic or a technician determines whether the mold is divided into multiple segments. If the mold is divided into multiple segments, the method continues to block 255. Otherwise, the method proceeds to block 250.

At block 250, the main body of the mold is removed from the shell. As mentioned, in an alternative embodiment, the main body may first be removed from the shell, followed by removal of one or more separable features.

At block 255, the mold is broken at one or more weakened regions joining at least one segment of the mold to at least one other segment of the mold. Various techniques may be used to break these weakened regions of the mold. In one embodiment, a user may simply break the mold at the weakened regions between segments by attempting to remove the main body of the mold from the shell. The weakened regions may be weakened such that the weakened regions will break from the application of force before enough force is applied to damage or permanently deform the shell.

In one embodiment, the weakened regions joining segments (and/or joining separable features to the main body) are broken after the shell has been formed over the mold (e.g., during the process of removing the mold from the shell). In another embodiment, the weakened regions joining segments and/or the weakened regions joining the separable features to the main body (e.g., to the segments) are broken during the process of forming the shell over the mold. For example, the weakened regions may be crushed by the application of pressure used to form the shell over the mold. In other embodiments, some weakened regions may be broken during the formation of the shell, and other weakened regions of the mold may be broken after the shell has been formed. For example, weakened regions that join segments of the main body may be broken during forming of the shell and weakened regions that join the separable features to the main body may be broken after forming of the shell.

At block 260, a first segment of the main body of the mold is removed from the shell. At block 265, a second section of the main body of the mold is removed from the shell. If there are additional sections, then each of the additional sections may also be separately removed from the shell.

Additional processing of the shell may then be performed, such as any further cutting of the shell (e.g., at a previously marked gingival cut line). Other additional processing may include polishing the shell, cleaning the shell, stamping the shell, etc. The shell may then be packaged and shipped.

Figure 3A:
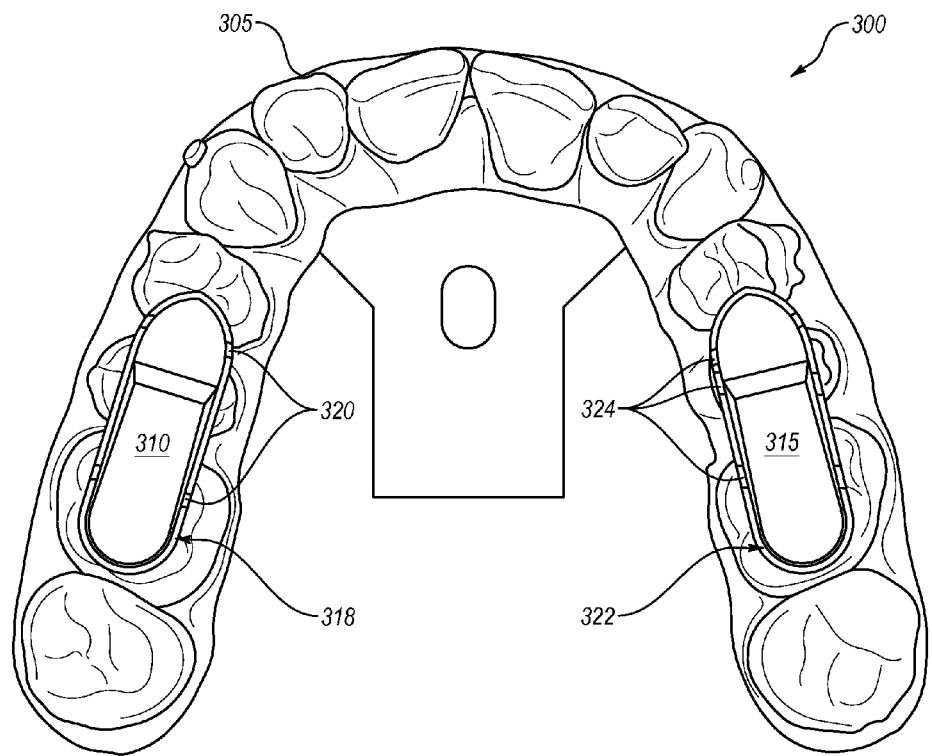
FIG. 3A illustrates a mold with separable features, in accordance with one embodiment.
Figure 3B:
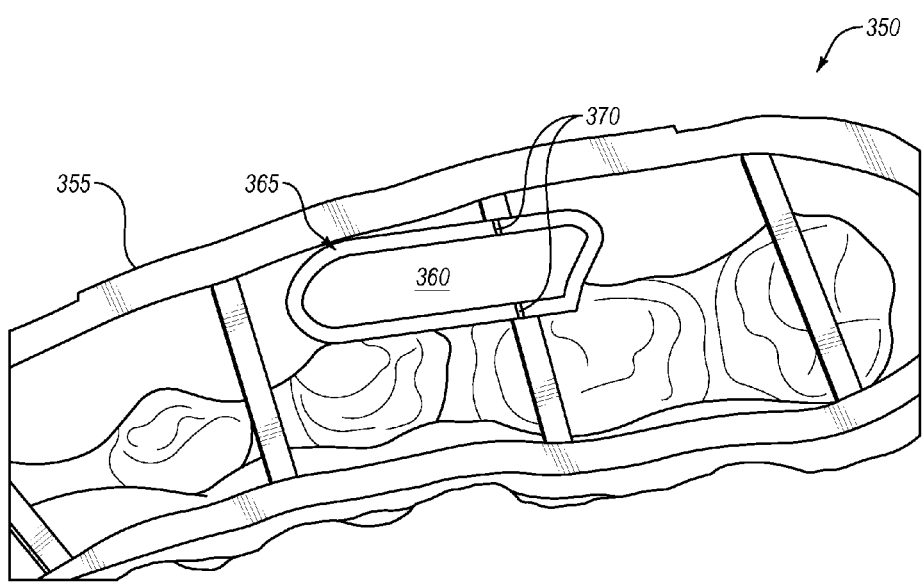
FIG. 3B illustrates a zoomed in view of a portion of a mold with a separable feature, in accordance with one embodiment.

FIG. 3A illustrates a top view of a mold 300 of a dental arch with a first separable feature 310 and a second separable feature 315. The first separable feature 310 is joined to a main body 305 of the mold 300 by a weakened region 318 that includes a void at a border of the first separable feature 310 and the main body 305 and support structures 320 that span the void. The weakened region that includes the void surrounds the first separable feature 310. The second separable feature 315 is joined to the main body 305 of the mold 300 by a weakened region 322 that includes a void at a border of the second separable feature 315 and the main body 305 and support structures 324 that span the void. The weakened region that includes the void surrounds the second separable feature 315. The main body 305, first separable feature 310, second separable feature 315 and support structures 320, 324 are all parts of a single contiguous mold. The weakened regions 318, 322 can be broken to enable the separable features to be removed from a shell separately from the main body (e.g., before the main body is removed).

FIG. 3B illustrates a bottom view of portion of a mold 350 of a dental arch with a separable feature 360. The separable feature 360 is joined to a main body 355 of the mold 350 by a weakened region 365 that includes a void at a border of the separable feature 360 and the main body 355 and support structures 370 that span the void. The weakened region that includes the void surrounds the separable feature 360. As shown, the separable feature 360 is accessible from the bottom of the mold while the mold is still attached to a shell formed thereon. Thus, a technician or machine may reach in and break the support structures 370 and then remove the separable feature from the shell without disturbing the main body 355.

Figure 3C:
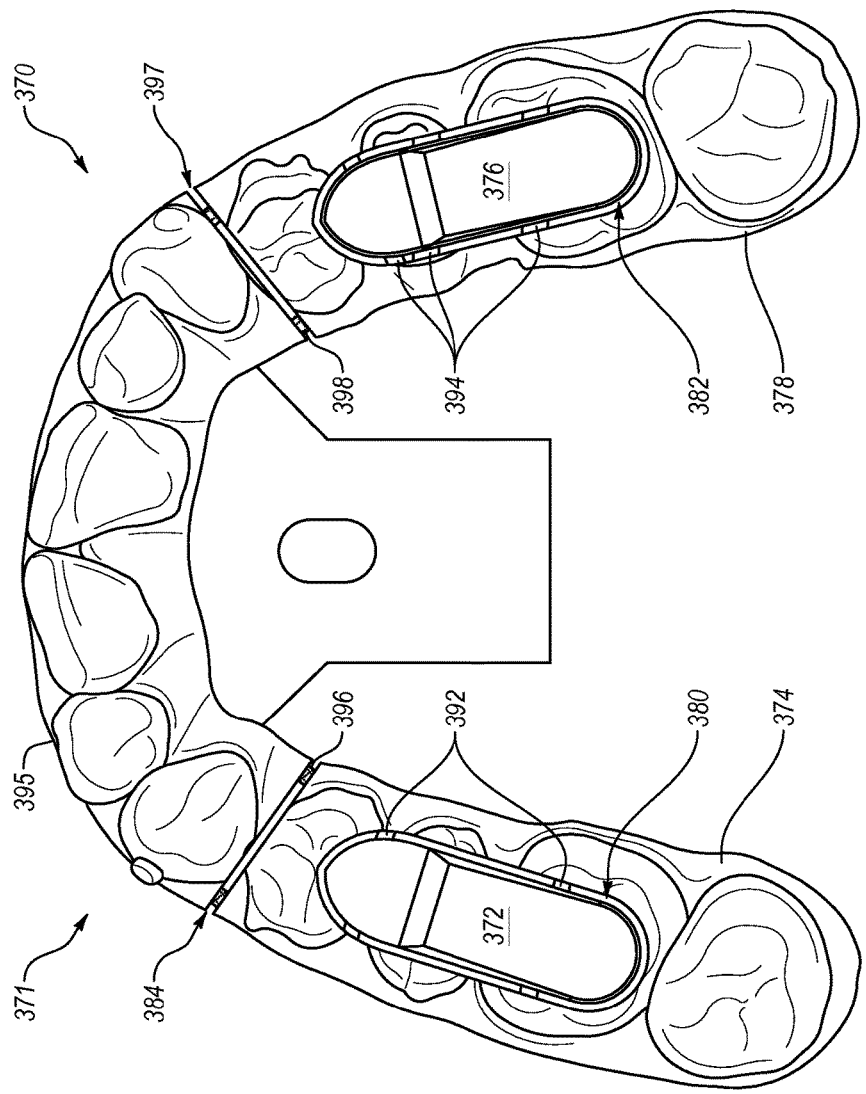
FIG. 3C illustrates a top view of a mold of a dental arch with a first separable feature attached to a first segment of a main body and a second separable feature attached to a second segment of the main body, in accordance with one embodiment.

FIG. 3C illustrates a top view of a mold 370 of a dental arch with a first separable feature 372 attached to a first segment 374 of a main body 371 and a second separable feature 376 attached to a second segment 378 of the main body 371. Mold 370 is substantially similar to mold 300 except for the division of the main body into multiple segments. The first separable feature 372 is joined to the first segment 374 by a weakened region 380 that includes a void at a border of the first separable feature 372 and the first segment 374 and support structures 392 that span the void. The second separable feature 376 is joined to the second segment 378 by another weakened region 382 that includes a void at a border of the second separable feature 376 and the second segment 378 and support structures 394 that span the void. The first segment 374 is joined to a third segment 395 by an additional weakened region 384 that includes a void at a border of the first segment 374 and the third segment 395 and support structures 396 that span the void. The second segment 378 is also joined to the third segment 395 by an additional weakened region 397 that includes a) a void at a border of the second segment 378 and the third segment 395 and b) support structures 398 that span the void. The first segment 374, second segment 378, third segment 395, first separable feature 372, second separable feature 382 and support structures 392, 394, 396, 398 are all parts of a single contiguous mold. The weakened regions 380, 382, 384, 387 can be broken to enable the separable features and the separate segments to be removed from a shell separately from one another.

Figure 4B:
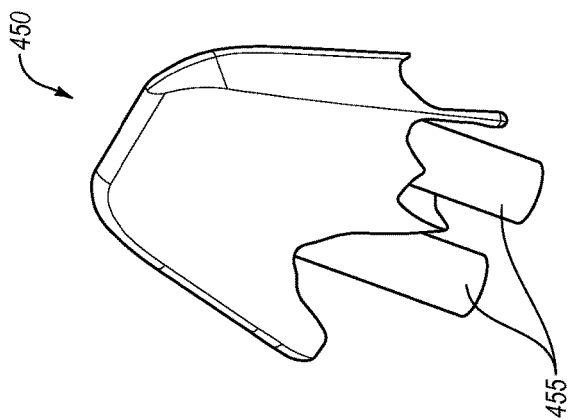
FIG. 4B illustrates a separable feature configured for placement in the mold of FIG. 4A, in accordance with one embodiment.
Figure 4A:
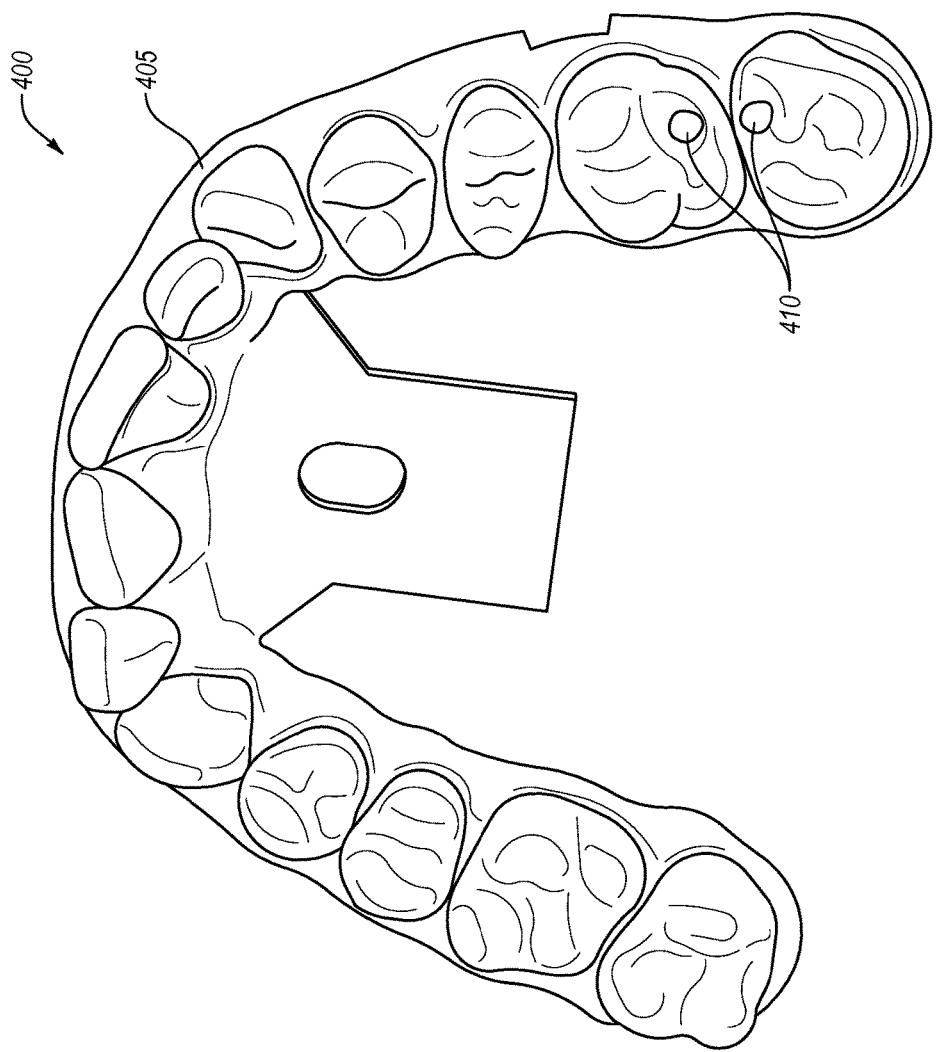
FIG. 4A illustrates a mold configured to receive a separable feature, in accordance with one embodiment.

FIG. 4A illustrates a top view of a mold 400 of a dental arch having a main body 405 and receiving elements (e.g., slots or holes) 410 that are configured to receive a separable feature, in accordance with one embodiment. FIG. 4B illustrates an additional mold of a separable feature 450 having protrusions 455 that are configured to be inserted into the receiving elements 410 on the mold 400, in accordance with one embodiment. The additional mold of the separable feature 450 may be attached to the mold 400 by placing the protrusions 455 into the receiving elements 410. After a shell has been formed over the mold 400 and the additional mold of the separable feature 450, the mold 400 may be removed from the shell, leaving behind the additional mold of the separable feature 450. The additional mold of the separable feature 450 may then be separately removed from the shell.

Figure 4C:
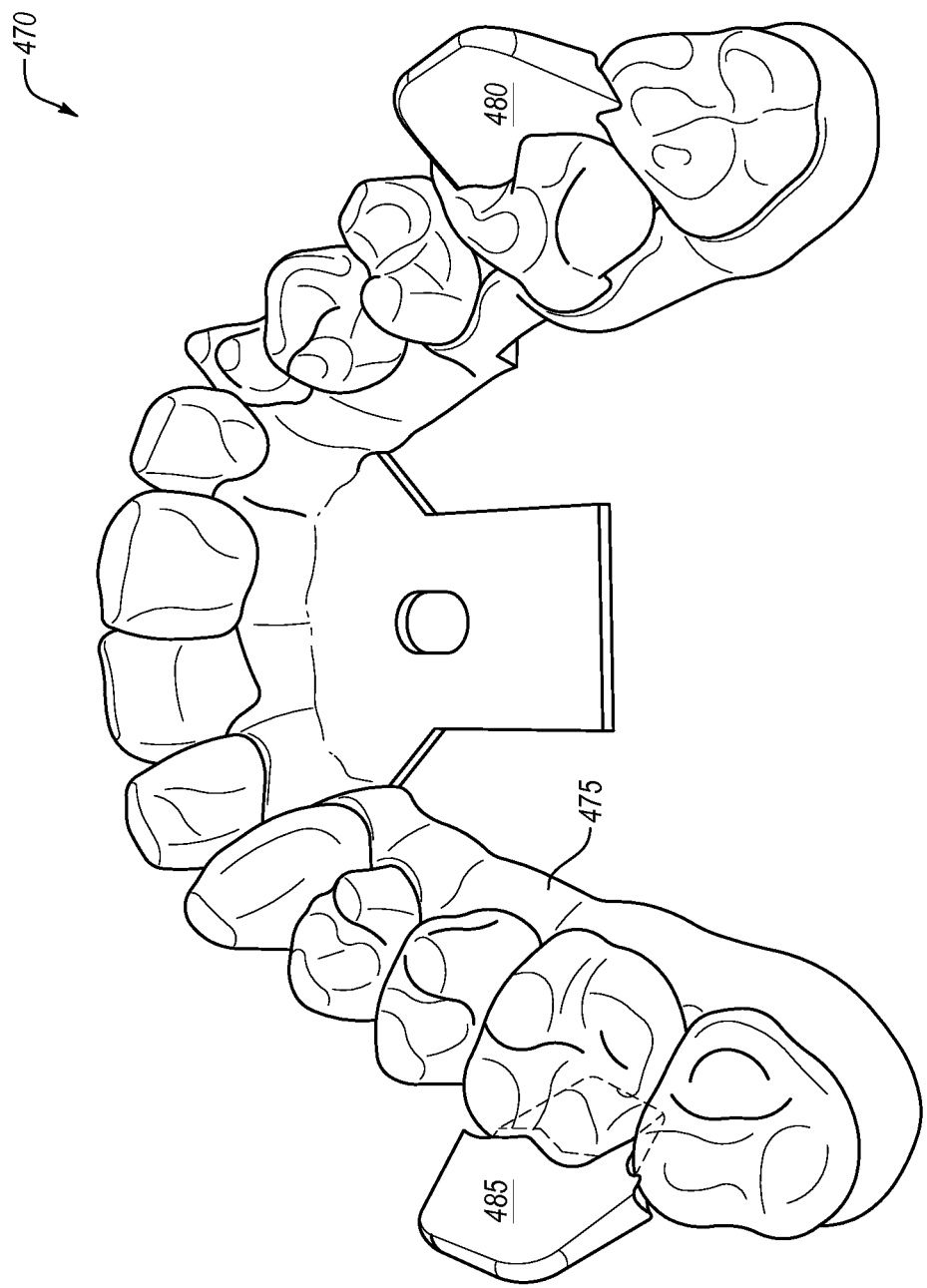
FIG. 4C illustrates another mold with separable features, in accordance with one embodiment.

FIG. 4C illustrates another mold 470 of a dental arch having a main body 475 and separable features 480, 485 that are mechanically affixed to the main body 475 via insertion into slots or other receiving elements in the main body 475.

Figure 4D:
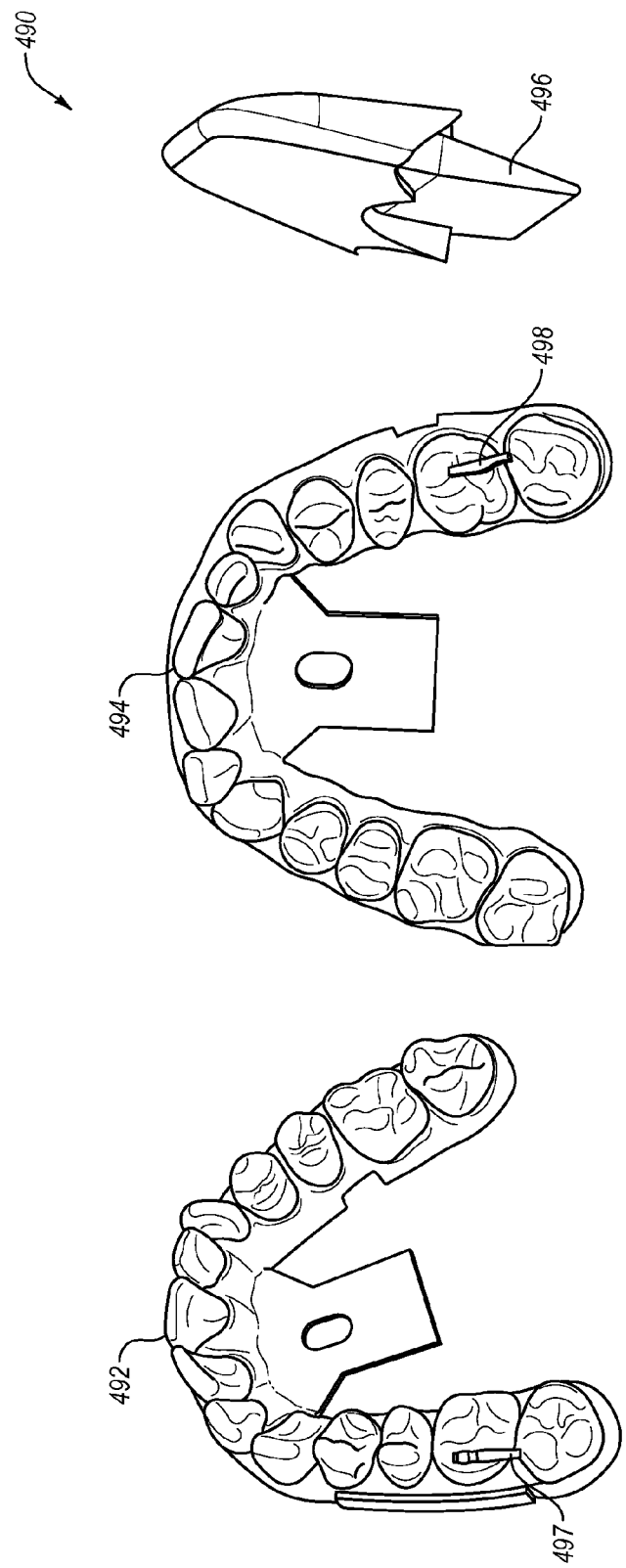
FIG. 4D illustrates additional molds with separable features, in accordance with one embodiment.

FIG. 4D illustrates a first mold 492 of a maxillary arch and a second mold 494 of a mandibular arch, each having a main body and slots for receiving a separable feature 496.

Figure 5A:
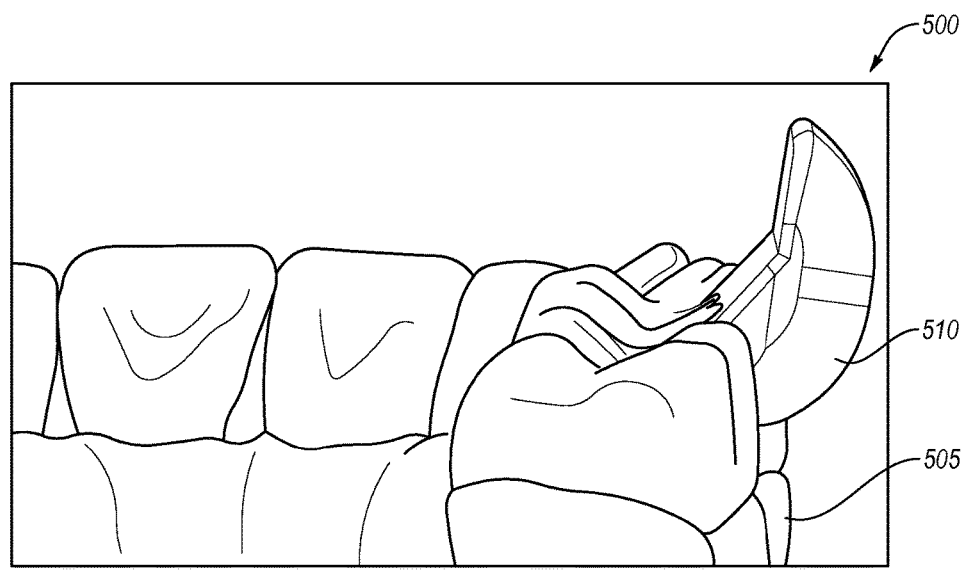
FIG. 5A illustrates an example mold of a dental arch with an attached feature.

FIG. 5A illustrates a mold 500 of a dental arch having a main body 505 with an attached feature 510. The attached feature 510 is large and retentive feature that has an undercut that could render removal of a shell formed over the mold 500 difficult if not impossible.

Figure 5B:
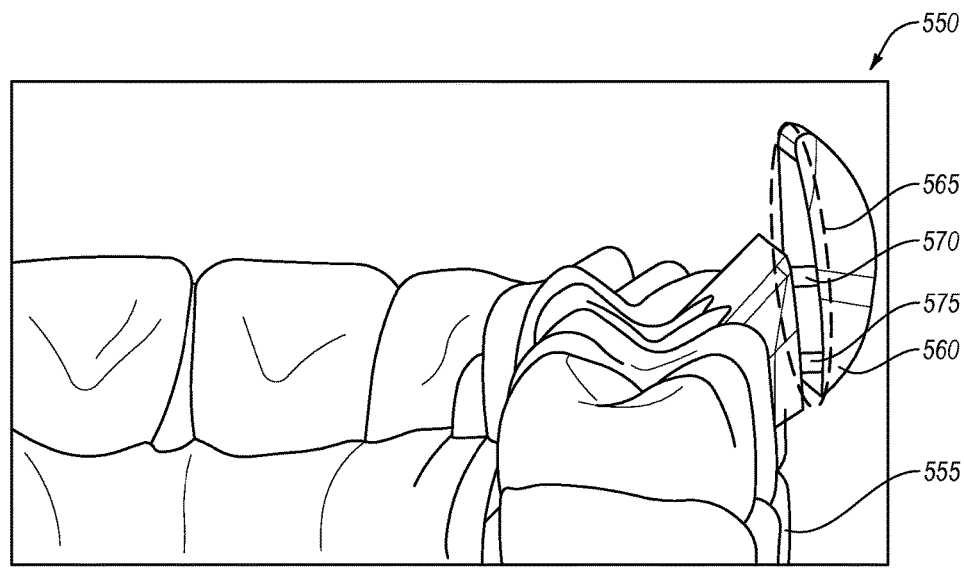
FIG. 5B illustrates an example mold of the dental arch of FIG. 5A with the inclusion of a separable feature, in accordance with one embodiment.

FIG. 5B illustrates an example mold 550 of the same dental arch of FIG. 5A with the addition of a separable feature 560. The mold 550 includes a main body 555 and an attached separable feature 560 (e.g. a feature that is similar to the attached feature 510 of FIG. 5A). However, separable feature 560 is joined to the main body 555 via a weakened region 565 that includes a void and two support structures 570, 575 that bridge the void. During removal of the mold 550 from a shell formed thereon, the support structures 570, 575 would break, enabling the main body 555 to be removed from the shell separately from the attached separable feature 560. This enables the mold 550 to be removed from the shell without damaging the shell.

FIG. 6 illustrates another example mold 600 with a separable feature 660. The example mold 600 includes a main body 655 that is joined to separable feature 660 by a weakened region 665. The weakened region 665 includes a void and three support structures 670-680 that bridge the void. Weakened region 665 may not reflect a size of an actual weakened region. For example, the illustrated weakened region 665 is shown with an enlarged void for the purpose of illustration. However, the width of this void may be reduced in some embodiments.

FIG. 7 illustrates an example breakable mold 700. The example breakable mold 700 is divided into a first section 755, a second section 760 and a third section 762. The first section 755 is joined to the second and third sections 760, 762 via a first weakened region 765 that includes a void and multiple support structures 770 that span the void. Second section 760 is additionally joined to third section 762 by a second weakened region 780 that includes a void and multiple support structures 785 that span the void. Weakened regions 765, 780 may not reflect sizes of actual weakened regions. For example, the illustrated weakened regions 765, 780 are shown with enlarged voids for the purpose of illustration. However, the width of these voids may be reduced in some embodiments.

Figure 8:
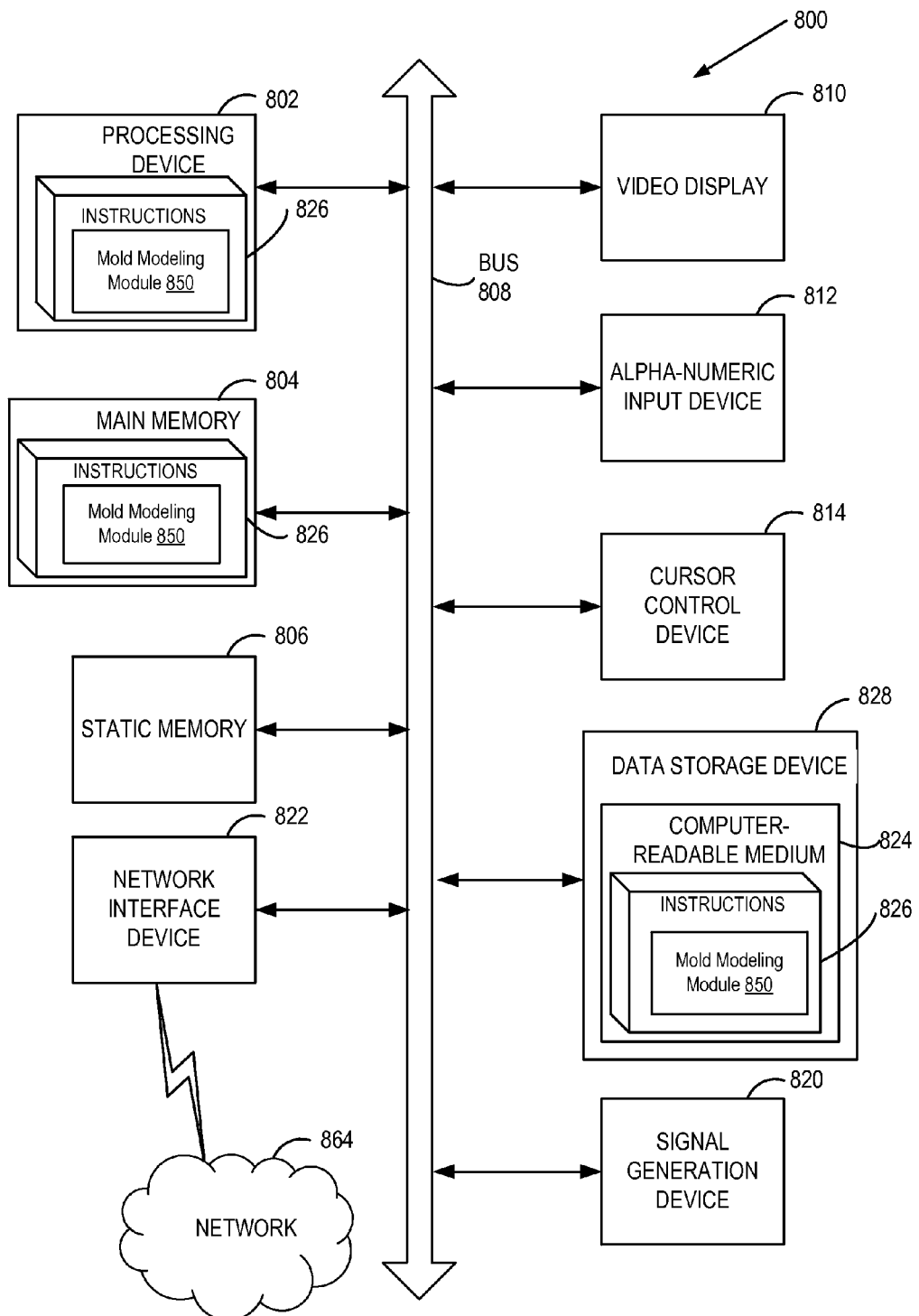
FIG. 8 illustrates a block diagram of an example computing device, in accordance with embodiments of the present invention.

FIG. 8 illustrates a diagrammatic representation of a machine in the example form of a computing device 800 within which a set of instructions, for causing the machine to perform any one or more of the methodologies discussed with reference to FIG. 1. In alternative embodiments, the machine may be connected (e.g., networked) to other machines in a Local Area Network (LAN), an intranet, an extranet, or the Internet. For example, the machine may be networked to a rapid prototyping apparatus such as a 3D printer or SLA apparatus. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 800 includes a processing device 802, a main memory 804 (e.g., read-only memory (ROM), flash memory, dynamic random access memory (DRAM) such as synchronous DRAM (SDRAM), etc.), a static memory 806 (e.g., flash memory, static random access memory (SRAM), etc.), and a secondary memory (e.g., a data storage device 828), which communicate with each other via a bus 808.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 826) for performing operations and steps discussed herein.

The computing device 800 may further include a network interface device 822 for communicating with a network 864. The computing device 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 820 (e.g., a speaker).

The data storage device 828 may include a machine-readable storage medium (or more specifically a non-transitory computer-readable storage medium) 824 on which is stored one or more sets of instructions 826 embodying any one or more of the methodologies or functions described herein. A non-transitory storage medium refers to a storage medium other than a carrier wave. The instructions 826 may also reside, completely or at least partially, within the main memory 804 and/or within the processing device 802 during execution thereof by the computer device 800, the main memory 804 and the processing device 802 also constituting computer-readable storage media.

The computer-readable storage medium 824 may also be used to store one or more virtual 3D models and/or a mold modeling module 850, which may perform one or more of the operations of method 100 described with reference to FIG. 1. The computer readable storage medium 824 may also store a software library containing methods that call a mold modeling module 850. While the computer-readable storage medium 824 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A method comprising:
   forming a shell over a mold comprising a separable feature, wherein the separable feature of the mold is joined to a main body of the mold by one or more first weakened regions, wherein the main body comprises a first section joined to a second section by one or more second weakened regions;
   separating the separable feature from the main body of the mold at the one or more first weakened regions;
   at least partially separating the first section from the second section at the one or more second weakened regions;
   removing the separable feature of the mold from the shell;
   separately removing the first section of the main body of the mold from the shell; and
   separately removing the second section of the main body of the mold from the shell.

2. The method of claim 1, wherein the mold comprises a 3D printed mold.

3. The method of claim 1, wherein the mold comprises a mold of a dental arch for a patient and the shell comprises at least one of an orthodontic aligner, an orthodontic retainer or an orthodontic splint to be used for at least one of aligning, retaining, or positioning one or more teeth of the patient.

4. The method of claim 1, wherein forming the shell comprises at least one of thermoforming or pressure forming the shell over the mold.

5. The method of claim 1, further comprising:
   identifying at least one of an undercut or a complex region that will be included in the mold;
   determining where in the mold to place the separable feature relative to at least one of the undercut or the complex region; and
   forming the mold.

6. The method of claim 5, wherein the one or more first weakened regions are formed during the forming of the mold.

7. The method of claim 5, further comprising:
   processing the mold after formation of the mold to introduce the one or more first weakened regions to the mold.

8. The method of claim 1, wherein the main body of the mold is breakable, the method further comprising:
   breaking the main body of the mold at the one or more second weakened regions to enable the first section to at least partially separate from the second section.

9. The method of claim 1, wherein the separable feature is retentive, and wherein the one or more weakened regions surround the separable feature.

10. The method of claim 1, further comprising:
    forming the main body;
    separately forming the separable feature; and
    securing the separable feature to the main body by the one or more first weakened regions prior to forming the shell.

* * * * *